(12) United States Patent
Liang

(10) Patent No.: US 12,582,515 B2
(45) Date of Patent: *Mar. 24, 2026

(54) METHODS AND DEVICES FOR REFRACTIVE CORRECTIONS OF PRESBYOPIA

(71) Applicant: Junzhong Liang, Fremont, CA (US)

(72) Inventor: Junzhong Liang, Fremont, CA (US)

( * ) Notice: Subject to any disclaimer, the term of this patent is extended or adjusted under 35 U.S.C. 154(b) by 756 days.

This patent is subject to a terminal disclaimer.

(21) Appl. No.: 18/051,842

(22) Filed: Nov. 1, 2022

(65) Prior Publication Data

US 2023/0083510 A1 Mar. 16, 2023

Related U.S. Application Data

(62) Division of application No. 16/862,188, filed on Apr. 29, 2020, now Pat. No. 11,529,228, which is a
(Continued)

(51) Int. Cl.
*G02C 7/04* (2006.01)
*A61F 2/14* (2006.01)
(Continued)

(52) U.S. Cl.
CPC ............ *A61F 2/147* (2013.01); *A61F 2/1613* (2013.01); *A61F 9/00808* (2013.01); *G02C 7/02* (2013.01); *G02C 7/028* (2013.01); *G02C 7/042* (2013.01); *G02C 7/044* (2013.01); *G02C 7/049* (2013.01); *G02C 7/061* (2013.01); *A61F 2/1618* (2013.01); *A61F 2/1637* (2013.01); *A61F 2/1643* (2015.04); *A61F 9/00812* (2013.01);
(Continued)

(58) Field of Classification Search
None
See application file for complete search history.

(56) References Cited

U.S. PATENT DOCUMENTS

| | | |
|---|---|---|
| 4,504,982 A | 3/1985 | Burk |
| 4,795,462 A | 1/1989 | Grendahl |

(Continued)

FOREIGN PATENT DOCUMENTS

| | | |
|---|---|---|
| EP | 1792562 A1 | 6/2007 |
| WO | 2004024035 A1 | 3/2004 |

(Continued)

OTHER PUBLICATIONS

European Search Report dated Oct. 14, 2016 for European Patent Application No. 16184643.1.
(Continued)

*Primary Examiner* — Darryl J Collins
(74) *Attorney, Agent, or Firm* — MLO, a professional corp.

(57) ABSTRACT

Methods for treating presbyopia in a patient's eye involve inducing spherical aberration in a central area of the pupil. In embodiments, refractive properties of an eye are measured to obtain a baseline refractive correction. A lens for wearing on the eye is provided to create spherical aberration or a distribution of spherical aberrations beyond the baseline refractive correction in the central area of the pupil. The central area of the pupil has a diameter of between 1.5 mm and 4.0 mm and has negligible spherical aberration without the treatment.

14 Claims, 13 Drawing Sheets

Related U.S. Application Data division of application No. 12/935,287, filed as application No. PCT/US2009/001980 on Mar. 31, 2009, now abandoned.

(60) Provisional application No. 61/072,653, filed on Apr. 2, 2008.

(51) Int. Cl.

| | |
|---|---|
| *A61F 2/16* | (2006.01) |
| *A61F 9/008* | (2006.01) |
| *G02C 7/02* | (2006.01) |
| *G02C 7/06* | (2006.01) |

(52) U.S. Cl.

CPC .............. *A61F 2009/00872* (2013.01); *A61F 2009/0088* (2013.01); *G02C 2202/22* (2013.01)

(56) References Cited

U.S. PATENT DOCUMENTS

| | | | |
|---|---|---|---|
| 5,089,024 | A | 2/1992 | Christie et al. |
| 5,089,204 | A | 2/1992 | Kitao et al. |
| 5,147,393 | A | 9/1992 | Van Noy et al. |
| 5,384,606 | A | 1/1995 | Koch et al. |
| 5,619,289 | A | 4/1997 | Seidner et al. |
| 5,652,638 | A | 7/1997 | Roffman et al. |
| 5,771,088 | A * | 6/1998 | Perrott ................... G02C 7/044 351/159.41 |
| 6,082,856 | A | 7/2000 | Dunn et al. |

| | | | |
|---|---|---|---|
| 7,261,412 | B2 | 8/2007 | Somani et al. |
| 8,647,383 | B2 | 2/2014 | Sanger et al. |
| 8,894,202 | B2 * | 11/2014 | Back ...................... G02C 7/041 351/159.08 |
| 2003/0199858 | A1 | 10/2003 | Schelonka |
| 2004/0156013 | A1 | 8/2004 | Lindacher et al. |
| 2005/0041203 | A1 | 2/2005 | Lindacher et al. |
| 2005/0043794 | A1 | 2/2005 | Geraghty et al. |
| 2005/0246015 | A1 | 11/2005 | Miller |
| 2006/0116763 | A1 | 6/2006 | Simpson |
| 2006/0238702 | A1 | 10/2006 | Glick et al. |

FOREIGN PATENT DOCUMENTS

| | | | |
|---|---|---|---|
| WO | 2007145082 | A1 | 12/2007 |
| WO | 2009058755 | | 5/2009 |
| WO | 2009058755 | A1 | 5/2009 |

OTHER PUBLICATIONS

Extended European Search Report dated Jun. 29, 2015 for EP Application 09727292.6-1651/2265216, PCT/US2009001980.

Notice of Allowance and Fees dated Aug. 12, 2022 for U.S. Appl. No. 16/862,188.

Office Action dated Feb. 16, 2022 for U.S. Appl. No. 16/862,188.

Office Action dated Jun. 23, 2017 for U.S. Appl. No. 12/935,287.

Office Action dated Sep. 28, 2017 for European Patent Application No. 16184643.1.

Supplementary Partial European Search Report dated Mar. 6, 2015 for European U.S. Appl. No. 09727292.

\* cited by examiner

FIG 1A
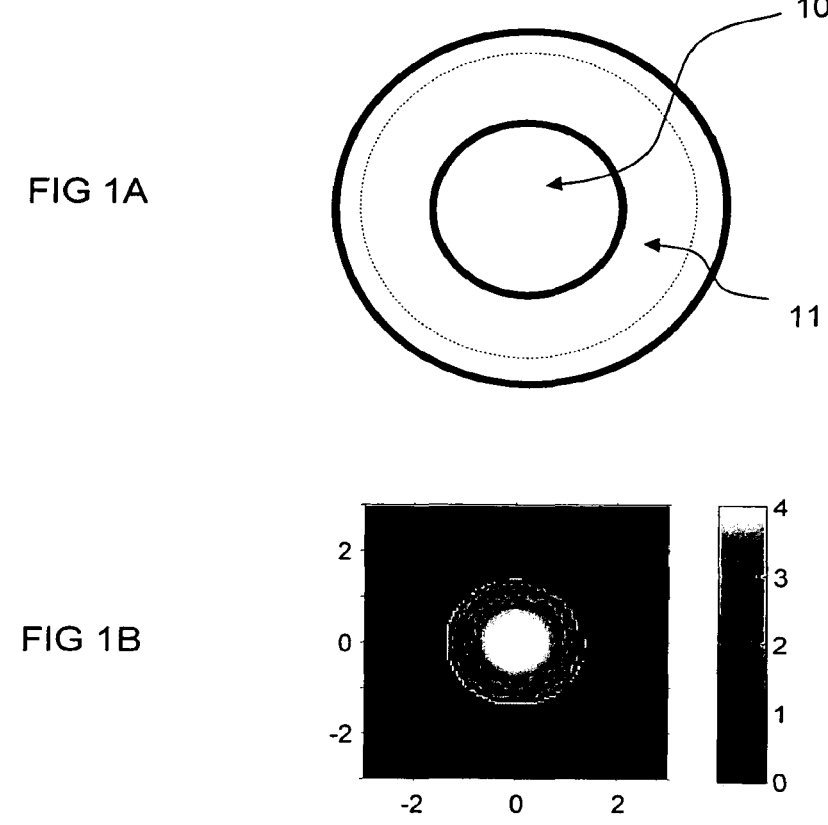
FIG 1B
FIG 1C
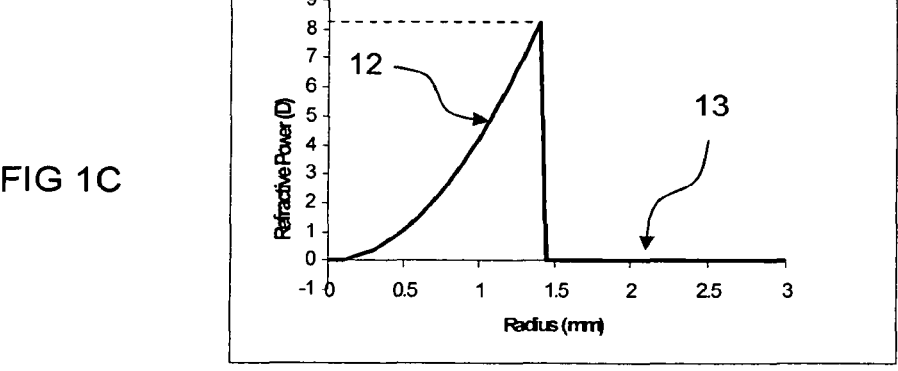

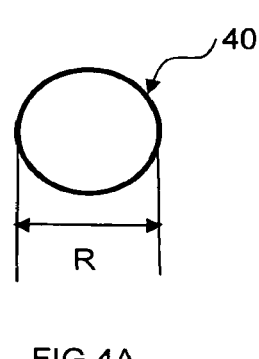
FIG 4A
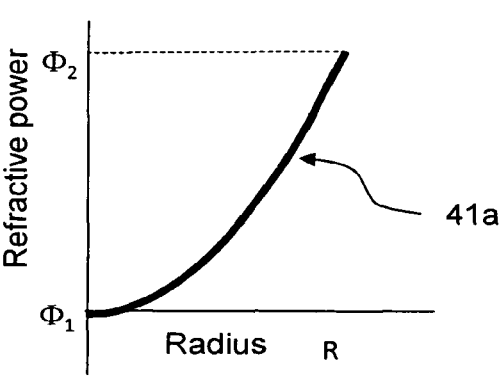
FIG 4B
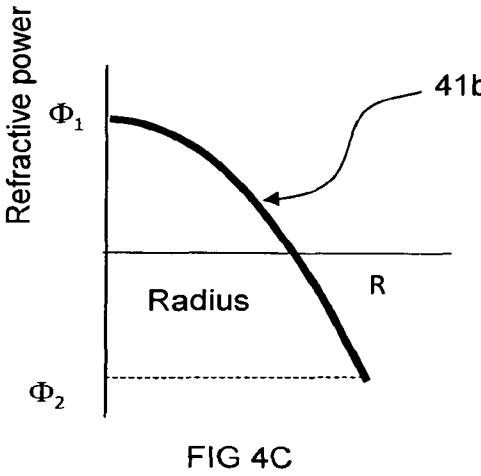
FIG 4C
FIG 4D

METHODS AND DEVICES FOR REFRACTIVE CORRECTIONS OF PRESBYOPIA

This application is a divisional of U.S. patent application Ser. No. 16/862,188, entitled "Methods and Devices for Refractive Corrections of Presbyopia," filed on Apr. 29, 2020; which is a divisional of U.S. patent application Ser. No. 12/935,287, entitled "Methods and Devices for Refractive Corrections of Presbyopia" and filed on Sep. 29, 2010; which claims priority to International Application No. PCT/US2009/001980, entitled "Methods and Devices for Refractive Corrections of Presbyopia" and filed on Mar. 31, 2009; which claims priority to U.S. Provisional Application No. 61/072,653 entitled "Methods and devices for treatments of presbyopia" and filed Apr. 2, 2008; which are all hereby incorporated by reference in their entirety.

FIELD OF THE INVENTION

The field of the invention relates to refractive correction of human eyes, in particular, for refractive treatments of presbyopia.

BACKGROUND OF THE INVENTION

Presbyopia is an age-related problem with near vision, due to progressive reduction in the eye's ability to focus, with consequent difficulty in reading at the normal distance. An effective refractive correction of presbyopia must provide focus for far, intermediate, and near vision in all conditions of pupil size.

Diffractive intraocular lenses (IOLs) such as those described in U.S. Pat. No. 5,116,111 by Michael Simpson and John Futhey and in US 2006/0116764A1 by Michael Simpson can provide simultaneous bi-focus (far vision and near vision) correction for presbyopia, but have two inherent disadvantages: Degraded night vision with night glare caused by light scattering at the junctions of diffractive zones in the lens surface, and a blind spot at intermediate distance between the far and near focus points.

Multifocal designs by controlling light distribution for far, intermediate, and near vision across different aperture size of a lens were proposed by Valdmar Portney in U.S. Pat. Nos. 5,225,858 and 6,557,998B2. These lens designs can perform better for intermediate vision than Simpson's diffractive IOLs, but are also known to be inferior for performance at near vision. Moreover, Portney's lenses fail to achieve their full potential as they are based on simple geometric ray tracing, without taking into account a diffraction effect of light propagation.

Aspheric lenses were also proposed in U.S. Pat. No. 6,923,539B2 by Michael Simpson and in U.S. Pat. Nos. 5,166,711 and 6,409,340B1 by Valdmar Portney. These lenses have a periodic refractive power distribution across a lens. While Simpson's lens can increase focus depth for a mono-focal lens as illustrated in FIG. 9 of U.S. Pat. No. 6,923,539B2, such lens is typically not suitable for presbyopic correction.

Spherical aberration across the pupil of an eye produces different focusing power at different pupil radii. Negative spherical aberration across pupil of an eye was proposed for mitigation of presbyopia by Seema Somani and Kingman Yee in U.S. Pat. No. 7,261,412 B2. There, the inventors noted that negative spherical aberration across the entire pupil can shift the center of the focus range from far to an intermediate distance because negative spherical aberration produces focus power for far vision at the pupil center to intermediate vision at the pupil periphery.

However, inducing spherical aberration across an entire pupil of an eye has at least two limitations for presbyopic corrections. First, the total amount of spherical aberration induced across the pupil cannot be too strong to cause nighttime symptoms such as glare and starburst, which is the one of the fundamental reasons why lenses with significant spherical aberration have not been used in multifocal IOLs and contact lenses for presbyopic treatments. Second, Somani and Yee's method in U.S. Pat. No. 7,261,412 B2 is typically not sufficient for presbyoic treatments because the small amount of spherical aberration across the entire pupil only shifts the center of focus range and does not increase focus depth. Still further, currently known methods of spherical aberration for presbyopic corrections have failed to address issues of induced nighttime symptoms (glare, starburst) and increase focus depth of an eye for far vision, intermediate vision and near vision, thus rendering such solutions less than desirable.

Consequently, although many configurations and methods for vision correction for treatment of presbyopia are known in the art, all or almost all of them suffer from one or more disadvantages. Thus, there is still a need to provide improved configurations and methods for vision correction for treatment of presbyopia.

SUMMARY OF THE INVENTION

The present inventive subject matter is drawn to methods and devices for refractive treatment of presbyopia.

According to one embodiment of the invention, a corneal implant device for surgical implantation between the layers and in the optic zone of a cornea of an eye for treatment of presbyopia comprises a solid transparent optic less than 6.5 mm in diameter, wherein when implanted in the eye spherical aberration or a distribution of spherical aberrations is created in the central pupil between 1.5 mm and 4.0 mm in diameter only by the presence of said device.

According to another embodiment of the invention, a procedure for treatment of presbyopia comprises the steps of measuring refractive properties of an eye; removing corneal tissue to create spherical aberration or a distribution of spherical aberrations in the central pupil of an eye less than 4 mm in diameter.

According to another embodiment of the invention, a lens for the treatment of presbyopia of an eye comprises an inner optical section of 1.5 mm to 4 mm in diameter that contains at least one aspheric surface to induce spherical aberration or a distribution of spherical aberrations in addition to a spherical focus power; an outer transparent optical section of 4 mm to 40 mm in diameter that is configured to have a dominant spherical focus power.

According to another embodiment of the invention, a lens for the treatment of presbyopia of an eye comprises an inner optical section of 1.5 mm to 3.6 mm in diameter, wherein the inner optical section contains at least one aspheric surface to create spherical aberration or a distribution of spherical aberrations in addition to a spherical focus power; an middle optical section with an outer diameter of 2.5 mm to 5 mm that is configured to be a bi-focal lens; and an outer optical section with an outer diameter of 4 mm to 40 mm that is configured to have a dominant focus power.

According to another embodiment of the invention, an optical device for refractive treatment of presbyopia comprises an inner transparent optical section that contains at least one aspheric surface to induce spherical aberration or a distribution of spherical aberrations in addition to a spherical focus power; a middle section that is configured to attenuate or block light energy; and an outer transparent optical section that is configured to have a dominant spherical focus power.

Various objects, features, aspects and advantages of the present invention will become more apparent from the following detailed description of preferred embodiments of the invention.

BRIEF DESCRIPTION OF THE DRAWING

FIG. 1A shows a front view of an eye's optics that is divided into two optical sections: a central optical zone and an outer optical zone.

FIG. 1B shows a wavefront map for a refractive correction of presbyopia in a method of introducing spherical aberration only at a central pupil section of an eye.

FIG. 1C shows the radial distribution of refractive power derived from the wavefront map in FIG. 1B.

FIG. 4A shows a schematic diagram of a refractive element to be implanted into an eye for refractive corrections of presbyopia.

FIG. 4B shows a radial distribution of refractive power for the refractive element in FIG. 4A in one embodiment.

FIG. 4C shows a radial distribution of refractive power for the refractive element in FIG. 4A in another embodiment.

FIG. 4D shows a radial distribution of refractive power for the refractive element in FIG. 4A in yet another embodiment.

DETAILED DESCRIPTION

Figure 1D:
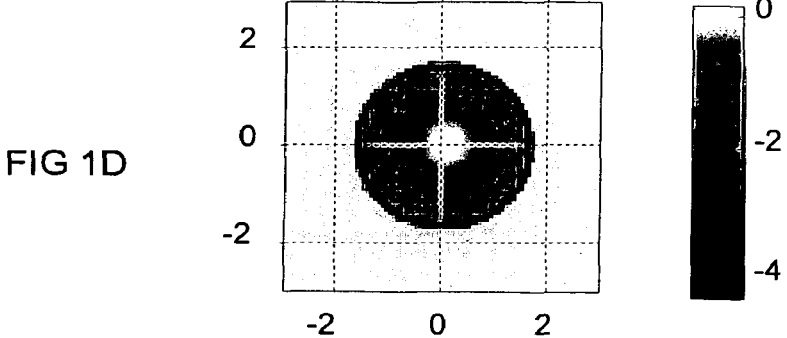
FIG. 1D shows a wavefront map for a refractive correction of presbyopia in a method of introducing a distribution of spherical aberrations only at a central pupil section of an eye.

Before describing wave front technologies for refractive correction of presbyopia, it must be emphasized that the refractive elements described in the present invention may include a baseline refractive correction of conventional refractive errors like myopia, hyperopia and astigmatism. For simplicity, the disclosed shapes (refractive powers and wavefront maps) only include the added wavefront map or refractive powers beyond the baseline correction for increasing focus depth from far vision to near vision.

I. Methods for Refractive Corrections of Presbyopia by Introducing Spherical Aberration or a Distribution of Spherical Aberrations Only at Pupil Center of an Eye FIG. 1A shows a schematic diagram of an eye's optics that is divided into two optical sections: the central optical section 10 less than 4.5 mm in diameter and the periphery pupil section 11 up to 8 mm in diameter. The dotted circle in FIG. 1A indicates the iris (pupil) of an eye at night. Diameter of an eye's pupil at night is different from eye to eye, and is smaller for aged eyes than for young eyes (typically 4 mm and 8 mm for night vision). For the central optical section less than 4.5 mm in diameter, it is well known that spherical aberration in normal human eyes is negligible. We describe methods for refractive correction of presbyopia by introducing positive/negative spherical aberration or a distribution of spherical aberrations only at the central pupil of an eye lens less than 4.5 mm in diameter.

In one embodiment, a negative (or positive) spherical aberration is introduced in the central optical section of an eye less than 4.5 mm in diameter only. An example is given in FIG. 1B, showing a wavefront map within a 6 mm zone. The wavefront shape, a negative spherical aberration of 4 microns within a diameter of 2.8 mm, can be expressed by Zernike polynomials as $-0.3(Z12(r)+3.87*Z4(r))$. Beyond the central 2.8 mm zone, the wavefront is constant because no spherical aberration will be introduced.

FIG. 1C shows the radial distribution of refractive power derived from the wavefront map in FIG. 1B. It is seen that the introduced negative spherical aberration increases (12) the refractive power from zero Diopters from pupil center to 8.2 Diopters at radius of 1.4 mm. Beyond the central zone, the refractive power is constant (13; zero in reference to a baseline refractive power). It must be emphasized that a baseline refractive correction of myopia, hyperopia or astigmatism can be superimposed to the refractive power shown in FIG. 1C for eyes with conventional refractive errors.

In another embodiment, a distribution of spherical aberrations is introduced in a central optical section of an eye less than 4.5 mm in diameter. An example is given in FIG. 1D, showing a wavefront map within a central optical zone of 3.6 mm in diameter. Instead of a single spherical aberration across a central pupil shown in FIG. 1B, this embodiment has two sections with different distributions of spherical aberration: an inner circular section of a diameter of 1.6 mm having a positive spherical aberration and an outer annular section of a diameter of 3.6 mm having a negative spherical aberration. The circular section of 1.6 mm has a positive spherical aberration about 1.34 um (or 0.1 ($Z12(r)+3.87 Z4(r)$) and also a focus offset of 4.0 Diopters. Outside the circular section, the annular section has a fixed focus power (0D) and a negative spherical aberration of about 4.3 um (or $-0.32 (Z12(r)+3.87 Z4(r)$).

Figure 1E:
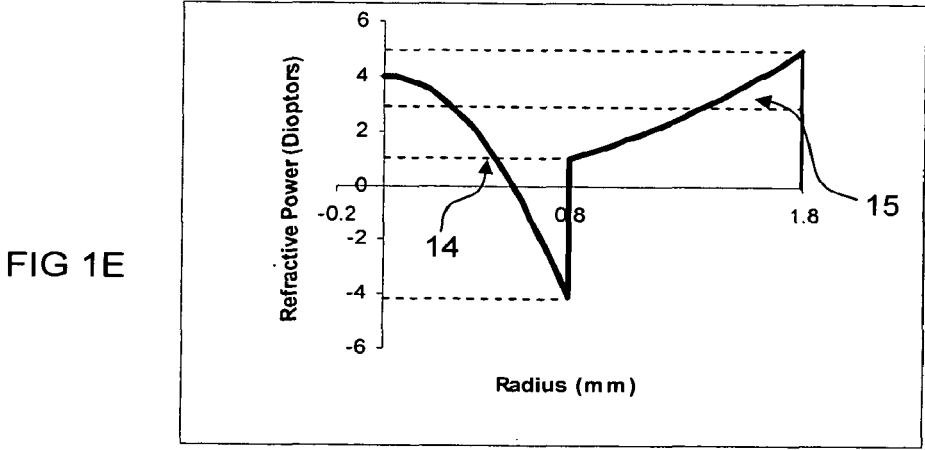
FIG. 1E shows the radial distribution of a refractive power derived from the wavefront map in FIG. 1D.

FIG. 1E shows the radial distribution of refractive power derived from the wavefront map in FIG. 1D. The positive spherical aberration in the central 1.6 mm pupil (0.8 mm in radius) causes a gradually reduced refractive power from the pupil center with a range of about 8 Diopters (14). The negative spherical aberration in an annual pupil causes a gradually increased refractive power from around 1 Diopter to around 5 Diopters (15). The wavefront map in FIG. 1D and the refractive power FIG. 1E show the central optical section with spherical aberrations only. Beyond the central 3.6 mm pupil, the wavefront as well as the refractive power is constant, which is not shown for simplicity.

Figure 2:
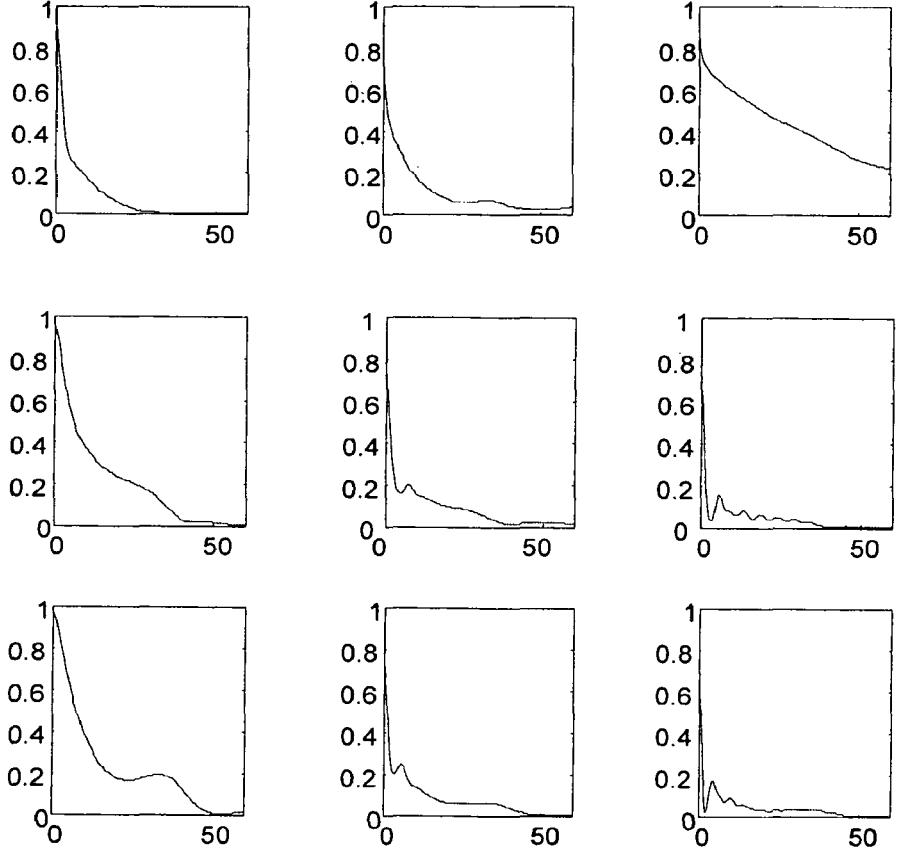
FIG. 2 shows the calculated MTFs (modulation transfer functions) of an eye with a wavefront map specified in FIG. 1B for three pupil sizes and at 3 different focus positions.

FIG. 2 shows the calculated MTFs of a hypothetical eye with a refractive correction specified by the wavefront in FIG. 1B. Three pupil sizes (2 mm, left column; 3.5 mm, middle column; and 6 mm, right column) and 3 distances (far vision at infinity, top; intermediate vision at a focus depth of 1.0 D, middle row; and near vision at a focus depth of 2.0 D, bottom row) are considered. Three important aspects of refractive corrections are noticed. First, the induced spherical aberration in the central pupil won't significantly degrade night vision with a large pupil for distant vision (top row and right column). Second, the induced spherical aberration by the refraction element at the central pupil can extend focus depth for an eye by up to 2 Diopters for pupil size less than 3.5 mm. Third, the benefit of improved focus depth is at a cost of degraded image quality for distance vision at a small (top row and right column) and medium (top row, middle column) pupil.

Figure 3:
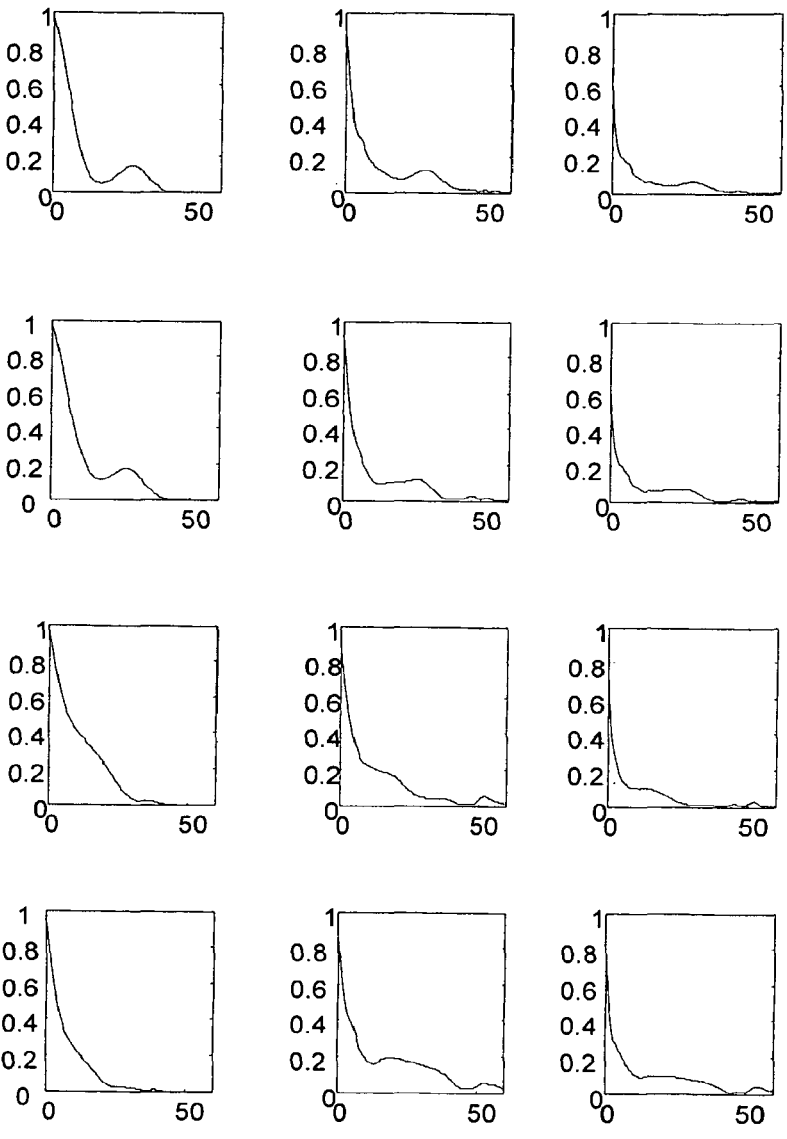
FIG. 3 shows the calculated MTFs of an eye with a wavefront map specified in FIG. 1D is for three pupil sizes and at 4 different focus positions.

FIG. 3 shows the calculated MTFs of a hypothetical eye with a refractive correction specified by the wavefront in FIG. 1D. Since increasing spherical aberration at central pupil won't significantly degrade night vision for a large pupil for distance vision as noticed in FIG. 2, we only calculate MTFs for three pupil sizes within a central 3.6 mm pupil. Three pupil sizes (1.6 mm, left column; 2.6 mm, middle column; and 3.6 mm, right column) and 4 distances (far vision at infinity, top row; intermediate vision at a focus depth of 1.0 D, second row; near vision at a focus depth of 2.0 D, third row; and near vision at a focus depth of 3 D, bottom row) are considered. Four aspects of refractive corrections are noticed with this embodiment of inducing a distribution of spherical aberrations and focus offsets in a central pupil. First, the refractive correction provides an excellent near vision for a pupil size between 2.6 mm and 3.6 mm. Second, the refractive correction provides excellent far vision for a small pupil between 1.6 mm and 2.6 mm. Third, the total focus depth is as large as 3 Diopters, which makes the embodiment suitable for all refractive correction devices, including contact lenses, spectacle lenses, IOLs, and intra-stroma refractive corneal inlay. Fourth, the benefit of improved focus depth is at a cost of degraded image quality for distance vision for a medium pupil size (top row and right column).

It is seen from FIG. 1A through FIG. 3 that engineering wavefront of an eye in the central pupil can achieve an increased focus depth up to 3 Diopters for pupil size within a 4 mm diameter. At night when the pupil size is larger, far vision can still be excellent if the optics in the outer pupil region beyond the central region maintains a focus at a far point (top row and right column in FIG. 2).

Inducing spherical aberration or a distribution of spherical aberrations in a central optical zone less than a 4.5 mm in diameter (FIG. 1B and FIG. 1D) for refractive treatments of presbyopia can be applied to a host of ophthalmic devices or procedures, including laser vision corrections, contact lenses, intraocular lenses, and refractive corneal inlays.

The wavefront maps in FIG. 1B and FIG. 1D can be obtained by superimposing the refractive power shown in FIG. 1C and FIG. 1E to a baseline refractive correction of myopia, hyperopia, or astigmatism, or equivalently by modifying optical path difference of a conventional lens according to a distribution of FIG. 1B and FIG. 1D.

For the procedure of laser vision correction (refractive correction by removing corneal tissues using laser energy), the wavefront maps in FIG. 1B and FIG. 1D can be obtained by modifying a baseline ablation profile for myopia, hyperopia, and astigmatism. The change in the ablation profile equals to $t0-W(x,y)/(nc-1)$, where t0 is a constant thickness, $W(x,y)$ is wavefront map (distribution), and nc is the refractive index of the cornea. Correction using a negative lens in conventional refractive correction must be implemented by removing a positive lens from a corneal for a laser vision correction.

For refractive corneal inlays that achieve refractive correction by altering corneal curvature, the wavefront maps like FIG. 1B and FIG. 1D can be obtained by varying thickness of an inlay according to $W(x,y)/(ni-1)$, where $W(x,y)$ is the desired wavefront map and ni is the refractive index of the corneal inlay. $W(x,y)$ can include a baseline of constant phase delay.

For contact lenses or spectacle lenses positioned outside the cornea of an eye, the wavefront maps like FIG. 1B and FIG. 1D can be obtained by superimposing the refractive power shown in FIG. 1C and FIG. 1E to a baseline refractive correction or to a constant phase delay across a lens.

For intra-ocular lenses or corneal inlays that do not alter curvature of optical surface of an eye, the wavefront maps like FIG. 1B and FIG. 1D can be obtained by a variation of thickness to the baseline lenses according to $W(x,y)/(nL-n0)$, where $W(x,y)$ is the wavefront map and nL is the refractive index of IOLs or corneal inlay while n0 is the refractive index of cornea or the refractive index of the aqueous humor or vitreous body in the eye.

We have described a number of ophthalmic devices for refractive correction of presbyopia based on the methods of introducing spherical aberration or a distribution of spherical aberrations at the central pupil in an eye. Exemplary ophthalmic devices can be found in the sections hereafter.

(a) Refractive Corneal Inlays for Refractive Treatments of Presbyopia

FIG. 4A shows a refractive corneal inlay for refractive correction of presbyopia in accordance with the present invention. The refractive device 40 comprises an optic of a diameter R between 1.5 mm and 4 mm, and has a radial distribution of refractive power in a range more than 4 Diopters across the optic.

In one embodiment as shown in FIG. 4B, the lens has the least refractive power in the middle ($\Phi1$), and a gradually increased refractive power for an increased radial distance, and a radial power range ($\Phi2$-$\Phi1$) of more than 4 Diopters and less than 12 Diopters. As an example, the lens in FIG. 4A has a diameter of 2.8 mm with a radial distribution of refractive power 41a same as 12 in FIG. 1B, and $\Phi1$ and $\Phi2$ are 0 Diopter and 8.2 Diopters, respectively. When such a lens is implanted into the central optics of an eye, it can create a wavefront map like the one shown in FIG. 1B because the implanted lens induces a negative spherical aberration in the central optical zone and does not alter refraction of an eye beyond the lens zone. Increasing focus depth of an eye for refractive correction of presbyopia can be seen in FIG. 2 for 3 pupil sizes at 3 different focus positions.

In another embodiment as shown in FIG. 4C, the lens has the highest refractive power in the middle ($\Phi1$), and a gradually reduced refractive power for an increased radial distance, and a radial power range ($\Phi2$-$\Phi1$) of more than 4 Diopters and less than 12 Diopters. As an example, the lens in FIG. 4A has a diameter of 1.6 mm with a radial distribution of refractive power 41b same as 14 in FIG. 1E, and $\Phi1$ and $\Phi2$ are 4 Diopter and −4.2 Diopters, respectively. When such a lens is implanted into the central optics of an eye, it creates a positive spherical aberration about 1 microns and a focus offset of 4D as described in our copending International application with the serial number PCT/US08/81421. Aberrations induced in the central pupil of the eye will increase focus depth of an eye by 2 to 3 Diopters for mitigation of presbyopia.

In yet another embodiment as shown in FIG. 4D, the lens has two radial distribution of refractive power: a first zone of reduced refractive power 42a and a second zone of increased refractive power 42b. As an example, the lens in FIG. 4A has a diameter of 3.6 mm with a radial distribution of refractive power 42a same as 14 in FIG. 1E, and 42b same as 15 in FIG. 1E. When such a lens is implanted into the central optics of an eye, it can create a wavefront map like the one shown in FIG. 1D at the central pupil and does not alter refraction of an eye beyond the lens zone. Increasing focus depth of an eye for refractive correction of presbyopia can be seen in FIG. 3 for 3 pupil sizes at 4 different focus positions.

In still another embodiment, a corneal inlay comprises an inner optical section of 1.5 mm to 4 mm in diameter that contains at least one aspheric surface to induce spherical aberration or a distribution of spherical aberrations in addition to a spherical focus power, and an outer transparent optical section of up to 6 mm in diameter. The corneal inlay will have a refractive power extended across the entire corneal inlay for refractive correction of conventional myopia, hyperopia, cylinder error, and any other refractive errors in an eye.

Figure 4E:
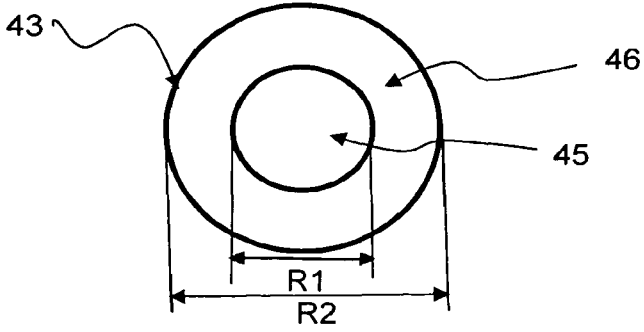
FIG. 4E shows schematic diagrams of a refractive element that can be worn on or implanted into an eye for refractive correction of presbyopia.
Figure 4E:
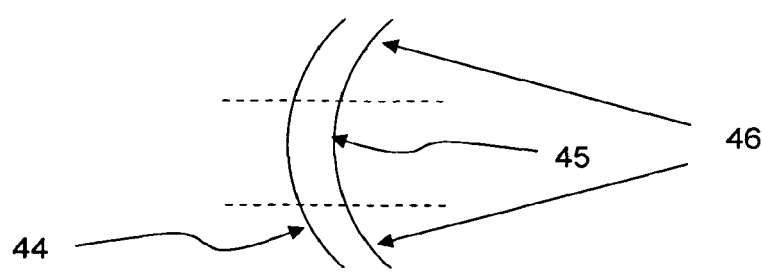

It must be mentioned that the refractive correction with a corneal inlay in FIG. 4A can also be implemented with a procedure of laser vision correction. Instead of inserting a lens that is described by the refractive power in FIG. 4B through FIG. 4E, a procedure of laser vision correction will remove corneal tissues to create a radial distribution of focus power of FIGS. 4C and 4E in an opposite sign, superimposed on to a baseline ablation profile for myopia, hyperopia, and astigmatism. A fixed ablation thickness can be added to the ablation profile beyond the central optical zone to avoid an abrupt change in ablation thickness.

(b) Ophthalmic Devices to be Worn on or Implanted into an Eye for Refractive Treatments of Presbyopia The refractive devices in FIG. 4A that induces spherical aberration or a distribution of spherical aberrations only at the central pupil of an eye can further include a periphery optical section to cover the entire pupil of an eye. FIG. 4E shows a schematic diagram of such an ophthalmic device 43 front view (44 side view). The device comprises a central optical section 45 (less than 4.5 mm in diameter) that has a radial distribution of refractive power in a range more than 4 Diopters, and an outer section 46 that has either a constant refractive power or a controlled spherical aberration beyond the central optical section.

Figure 4F:
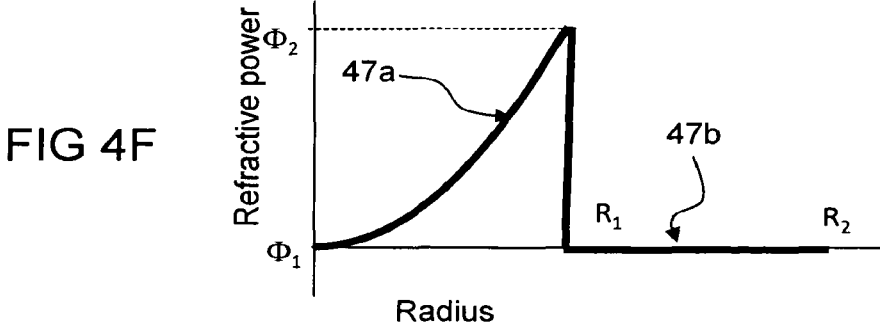
FIG. 4F shows a radial distribution of refractive power for the refractive element in FIG. 4E in one embodiment that has a gradually increased refractive power in the central optical section and a constant refractive power beyond the central optical section.
Figure 4G:
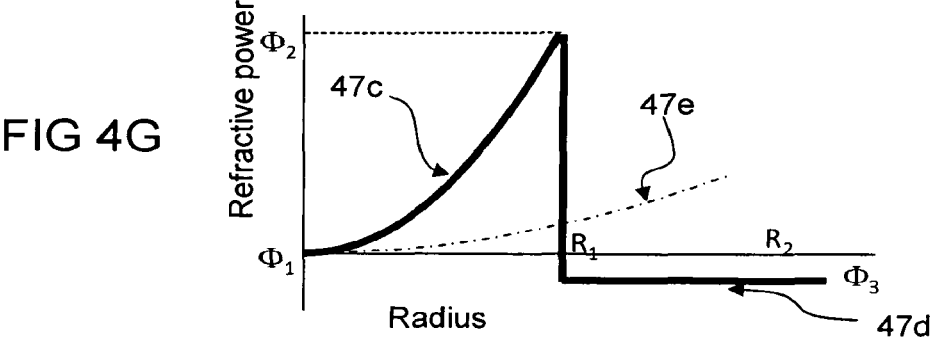
FIG. 4G shows a radial distribution of refractive power for the refractive element in FIG. 4E in an embodiment that has a gradually increased refractive power in the central optical section and a custom focus offset, depending on spherical aberration in an individual eye, beyond the central optical section.
Figure 4H:
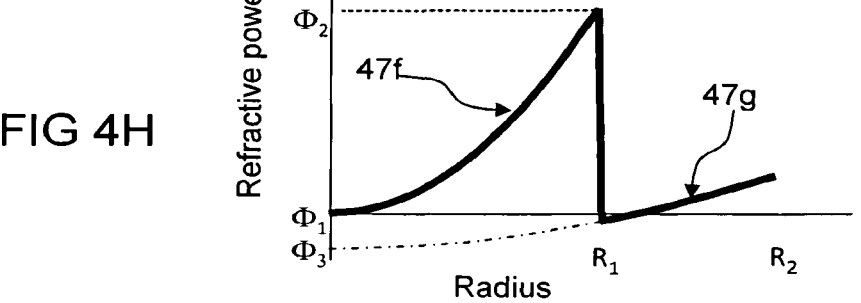
FIG. 4H shows a radial distribution of refractive power for the refractive element in FIG. 4E in one embodiment that has a gradually increased refractive power in the central optical section and a different radial distribution of refractive power beyond the central optical section.

In the embodiments shown in FIG. 4F through FIG. 4H, the central optical section (47a, 47c, and 47f) has a gradually increased refractive power from the middle of the lens same as that of 41a in FIG. 4b. In one embodiment shown in FIG. 4F, the outer segment 47b does not change spherical aberration in an eye and has a refractive power same as a baseline refractive correction. In another embodiment shown in FIG. 4G, the outer segment 47d has a negative focus offset from a baseline refractive correction to optimize night vision for an eye with negative spherical aberration at pupil periphery 47e. The negative focus offset at 47d can improve far vision at night by shifting refractive power at pupil periphery close to zero Diopter. In yet another the embodiment shown in FIG. 4H, the outer segment 47g contains spherical aberration to shift the refractive power close to zero Diopter for increased focus depth for night vision.

Figures 4I, 4J, 4K:
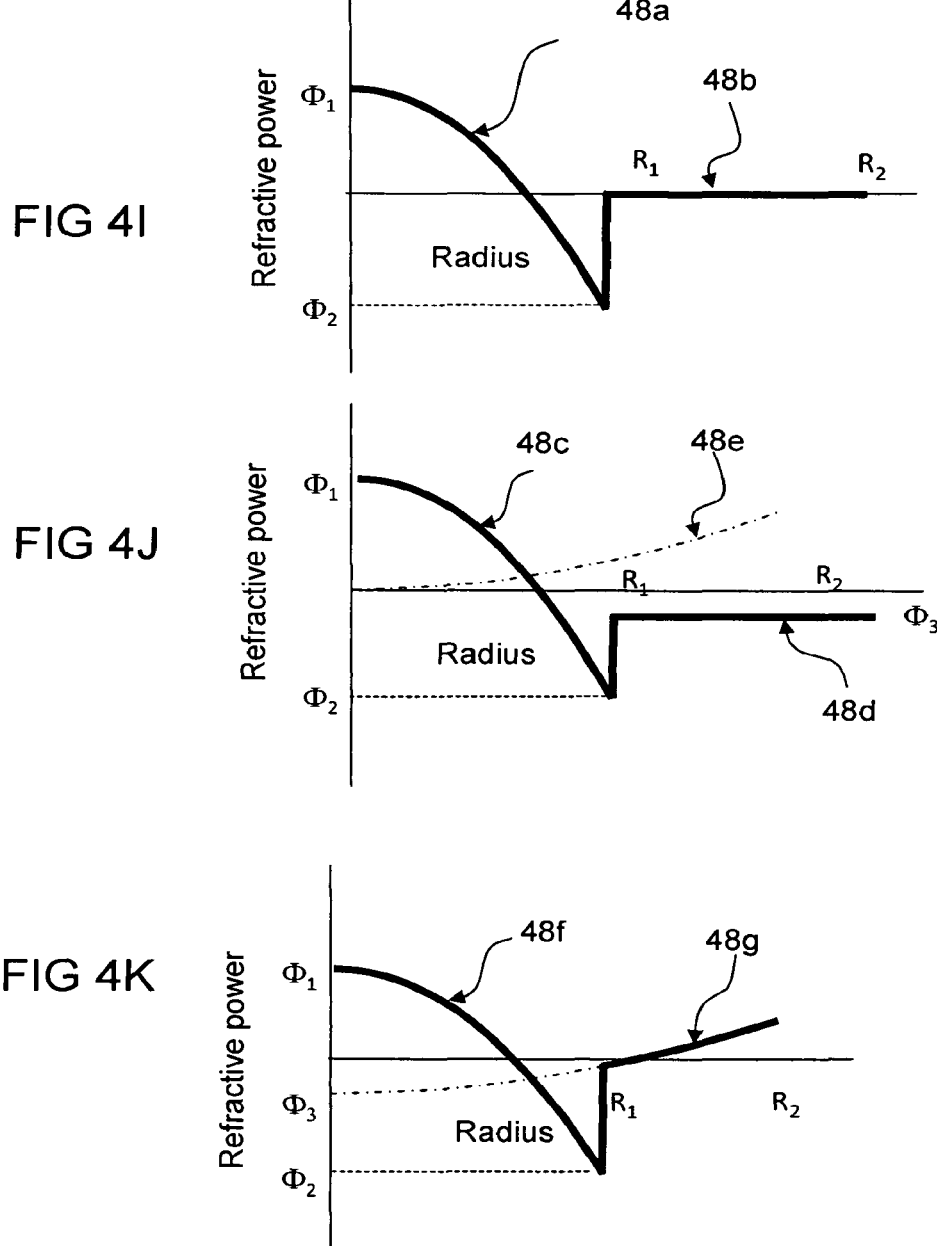
FIG. 4I shows a radial distribution of refractive power for the refractive element in FIG. 4E in one embodiment that has a gradually reduced refractive power in the central optical section and a constant refractive power beyond the central optical section.
FIG. 4J shows a radial distribution of refractive power for the refractive element in FIG. 4E in an embodiment that has a gradually reduced refractive power in the central optical section and a custom focus offset, depending on spherical aberration in an individual eye, beyond the central optical section.
FIG. 4K shows a radial distribution of refractive power for the refractive element in FIG. 4E in one embodiment that has a gradually reduced refractive power in the central optical section and a different radial distribution of refractive power beyond the central optical section.

In the embodiments shown in FIG. 4I through FIG. 4K, the central optical section (48a, 48c, and 48f) has a gradually decreased refractive power from the middle of the lens same as that of 41b in FIG. 4c. In one embodiment shown in FIG. 4I, the outer segment 48b does not change spherical aberration in an eye and has a refractive power same as a baseline refractive correction. In another embodiment shown in FIG. 4J, the outer segment 48d has a negative focus offset from a baseline refractive correction to optimize night vision for an eye with negative spherical aberration at pupil periphery 48e. The negative focus offset at 48d will improve far vision at night by shifting refractive power at pupil periphery close to zero Diopter. In yet another embodiment shown in FIG. 4K, the outer segment 48g contains spherical aberration to shift the refractive power close to zero Diopter for increased focus depth for night vision.

Figures 4L, 4M, 4N:
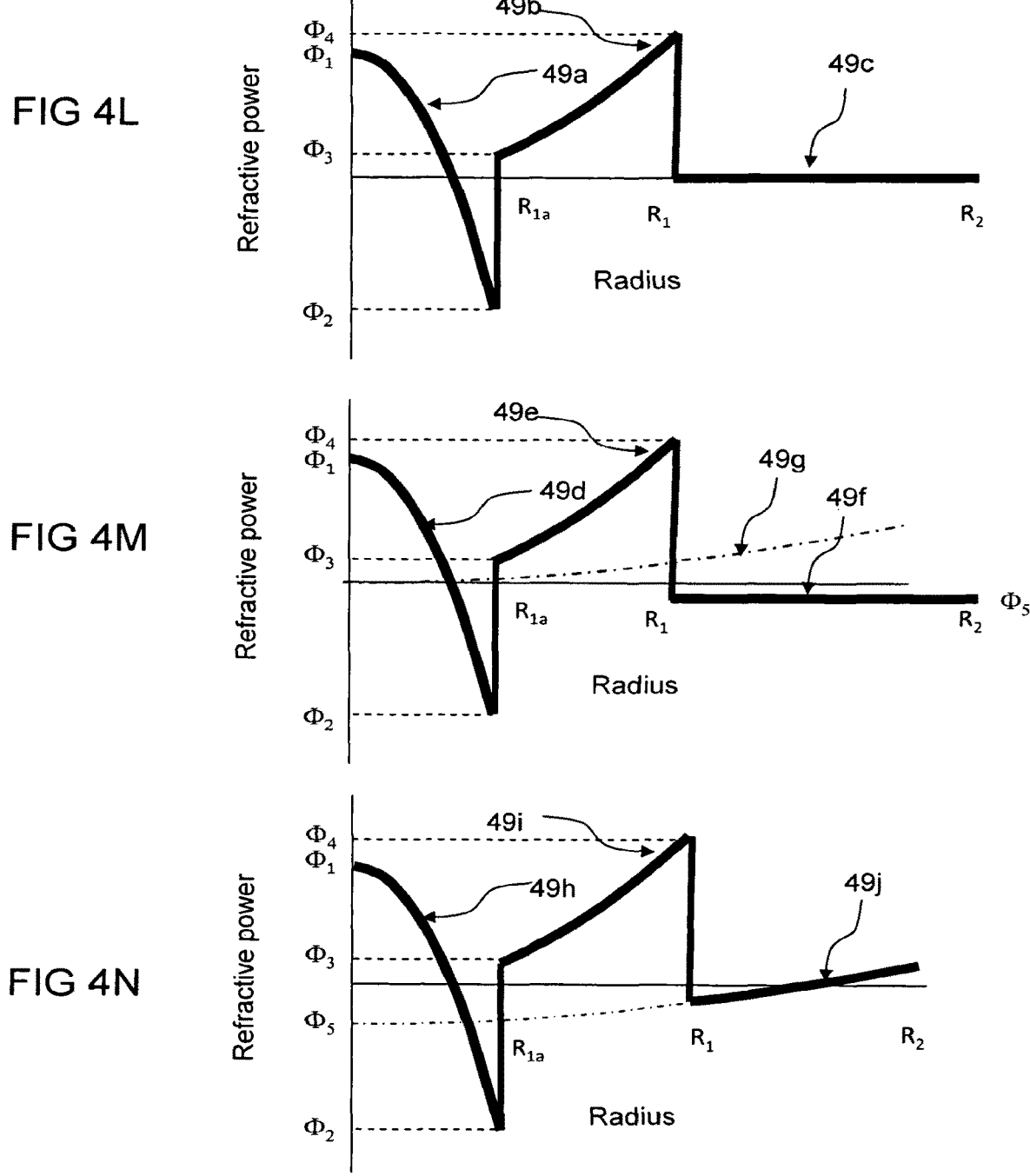
FIG. 4L shows a radial distribution of refractive power for the refractive element in FIG. 4E in one embodiment that has a first zone of reduced refractive power and a second zone of increased refractive power in the central optical section, and a constant refractive power beyond the central optical section.
FIG. 4M shows a radial distribution of refractive power for the refractive element in FIG. 4E in an embodiment that has a zone of reduced refractive power and a zone of increased refractive power in the central optical section, and a custom focus offset, depending on spherical aberration in an individual eye, beyond the central optical section.
FIG. 4N shows a radial distribution of refractive power for the refractive element in FIG. 4E in one embodiment that has a zone of reduced refractive power and another zone of increased refractive power in the central optical section, and a different radial distribution of refractive power beyond the central optical section.

In the embodiments shown in FIG. 4L through FIG. 4N, the central optical section has two distributions of refractive power: a zone of reduced refractive power (49a, d, h) and a zone of increased refractive power (49b, e, i) as 42a and 42b in FIG. 4d. In the embodiment shown in FIG. 4L, the outer segment 49c does not change spherical aberration in an eye and has a refractive power same as a baseline refractive correction. In the embodiment shown in FIG. 4M, the outer segment 49f has a negative focus offset from a baseline refractive correction to optimize night vision for an eye with negative spherical aberration at pupil periphery 49g. The negative focus offset at 49f will improve far vision at night by shifting refractive power at pupil periphery close to zero Diopter. In the embodiment shown in FIG. 4N, the outer segment 49j contains spherical aberration to shift the refractive power close to zero Diopter for increased focus depth for night vision.

When the devices in FIG. 4A and FIG. 4e are used as a refractive cornea inlay implanted into the corneal stroma, the device may include tiny holes in the optic to enable proper flow of nutrients from one side of the lens to the other side. The materials for making a corneal inlay may include hydrogel as well as those known in the art (see e.g., U.S. Pat. No. 5,336,261 by Graham D. Barrett, William J. Link, and Cary J. Reich). Implanting a refractive corneal inlay may be combined with a LASIK procedure for patients with conventional myopia, hyperopia, and astigmatism.

Lenses with induced spherical aberration in the central optic will involve in manufacturing of aspheric lenses because spherical aberration are often negligible for a small numerical aperture. Aspheric lenses can be made in a number of methods known in the prior art: 1) by machining a lens of aspheric surface (surfaces) with a lathe tool, 2) by molding lenses with an aspheric mold; 3) by an ablation or activation process using laser beams or radiation beams.

It must be mentioned that the refractive correction for lenses in FIG. 4F through 4N can also be implemented for laser vision corrections by removing corneal tissues. By superimpose the distributions of refractive power to a baseline refractive correction, ablation profiles can easily be generated for the corrections of not only myopia, hyperopia, astigmatism, but also presbyopia. Materials removed from the cornea for presbyopia needs to be equal to the t0−W (x,y)/(n−1) where t0 is a constant thickness, W(x,y) is the spherical aberration needed for presbyopia, and n is the refractive index of corneal.

Figure 5A:
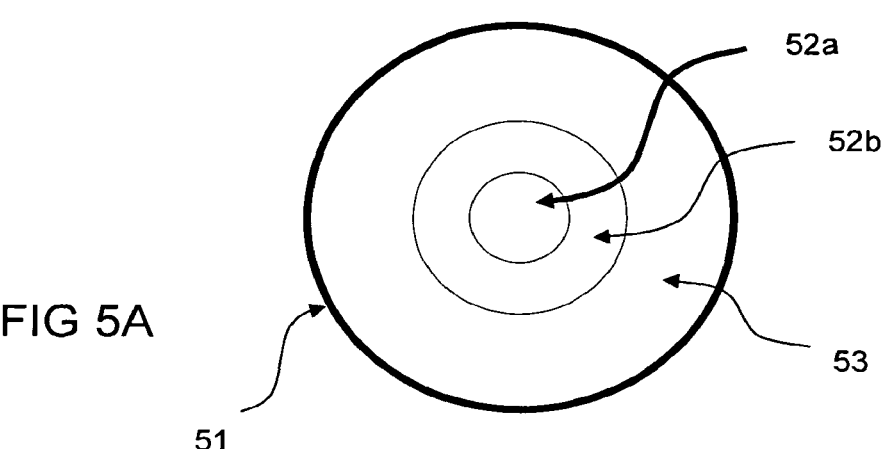
FIG. 5A shows a schematic diagram of a refractive element to be worn on or implanted in an eye for refractive correction of presbyopia.

(c) Refractive Correction of Presbyopia by Introducing a Distribution of Spherical Aberrations and Focus Offsets at Central Pupil of an Eye FIG. 5A shows a schematic diagram of yet another refractive element 51 to be worn on or implanted in the eye for refractive correction of presbyopia. The refractive element comprises at least two central aspheric segments 52a and 52b that create a distribution of spherical aberrations and focus offsets within a zone less than 4.5 mm in diameter, and an outer optical segment 53 that extends the optic beyond the central zones and up to 50 mm in diameter.

It must be emphasized that the refractive element may contain not only a baseline correction of myopia, hyperopia and astigmatism, but also a distributed spherical aberration in the central pupil of an eye.

The central aspheric segments 52a and 52b comprise at least two refractive surfaces, and at least one of the two refractive surfaces in both 52a and 52b is aspheric to create spherical aberration in a small numerical aperture within which conventional spherical refractive surfaces will have negligible spherical aberration.

When placed in the optical path of an eye, the refractive element superimposes a wavefront shape like the one shown in FIG. 1D at central pupil of an eye to a baseline correction for myopia, hyperopia and astigmatism across entire pupil of an eye if necessary. As indicated in FIG. 3, the induced distribution of spherical aberrations and focus offsets can achieve a focus depth of 3D in a pupil size within 3.6 mm without accommodation from the crystalline lens in an eye.

The outer optical segment 53 is transparent to light wave and has an outer diameter of 5 mm to 7 mm for implantable lenses like Intra-Ocular Lenses (IOLs), 10 to 14 mm in diameter for contact lenses, and up to 50 mm for spectacles.

Figure 5B:
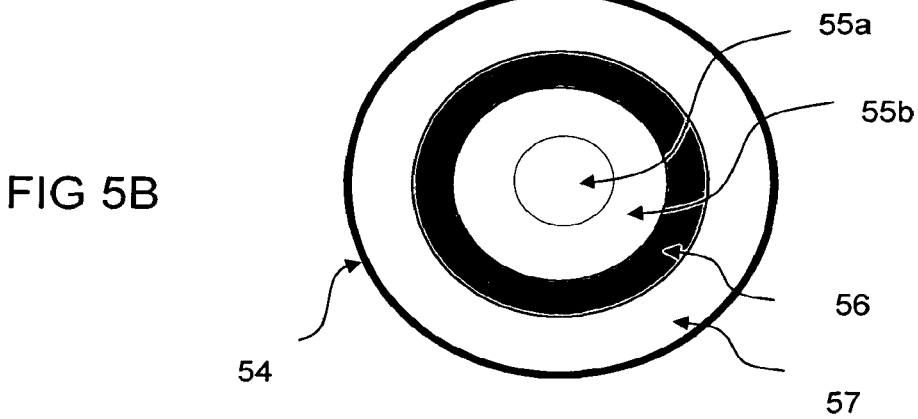
FIG. 5B shows a schematic diagram of another refractive element to be worn on or implanted in an eye for refractive correction of presbyopia.

FIG. 5B shows a schematic diagram of another refractive element 54 to be worn on or implanted in an eye for refractive correction of presbyopia. The refractive element comprises at least two central aspheric segments 55a and 55b that create a distribution of spherical aberrations and focus offsets within a zone less than 4.5 mm in diameter, and a light attenuate section 56 outside the aspheric sections, and an outer optical segment 57 that is extended the refractive element beyond the central zones and up to 14 mm in diameter.

Figure 5C:
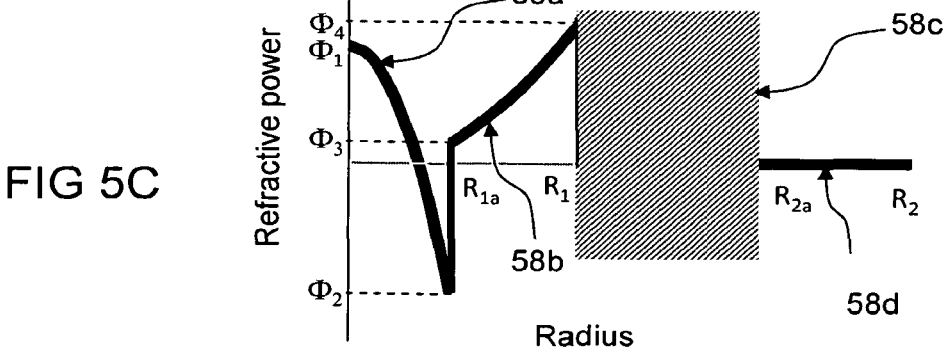
FIG. 5C shows a radial distribution of refractive power for a refractive element in FIG. 5B in one embodiment.

The difference between the refractive elements in FIG. 5A and in FIG. 5B is the inclusion of the light attenuating section 56 between the central aspheric section 55b and the outer section 57. FIG. 5C shows a distribution of refractive power with 58a and 58b as the two aspheric sections, light trough the shades section 58c will be blocked or attenuated, and a zone 58d with a constant refractive power.

The light attenuating section 56 (58c) can reduce or block light in an annular pupil section between ~3 mm and ~6 mm in order to reduce or eliminate impacts of high-order aberrations in individual eyes. Adding the light attenuating section can make the refractive element suitable for a variety of eyes with different high-order aberrations, and thus improve efficiency and efficacy of a refractive procedure.

II. Refractive Correction of Presbyopia by Introducing a Distribution of Spherical Aberrations and Focus Offsets Across Pupil of an Eye Increasing focus depth of an eye can also be achieved by a refractive element comprising of a plurality of optical sections with a distributed focus powers and spherical aberrations across pupil of an eye.

Figures 6A, 6B:
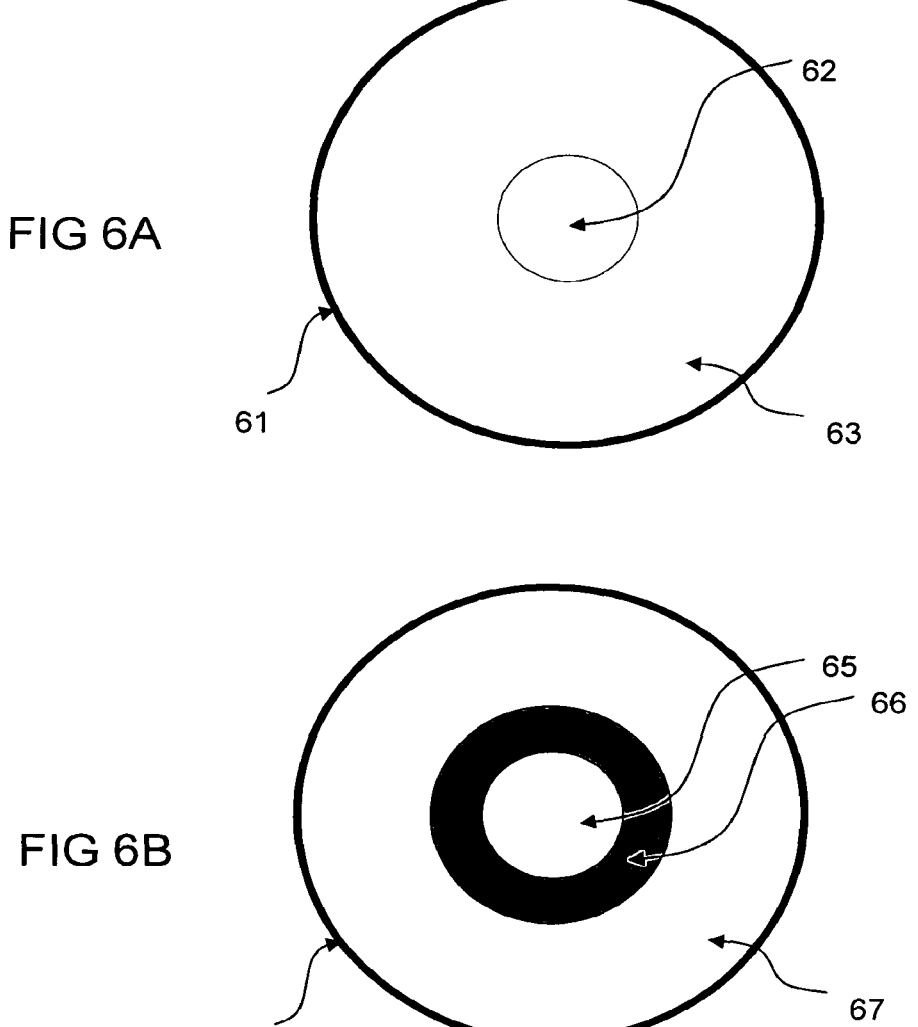
FIG. 6A shows a schematic diagram of yet another refractive element to be worn on or implanted in an eye for refractive correction of presbyopia.
FIG. 6B shows a schematic diagram of an additional refractive element to be worn on or implanted in an eye for refractive correction of presbyopia.

FIG. 6A shows a schematic diagram of such an embodiment of a refractive element 61 to be worn on or implanted in an eye for refractive correction of presbyopia. The central optical section 62 has one refractive power Φc, and is an aspheric lens to create spherical aberration Cc in a small numerical aperture. The diameter of the central optical section is between 1.6 mm and 4 mm. The outer optical section 63 has a different refractive power Φo from the central optical section, and a different spherical aberration Co.

When the refractive element is placed in the optical path of an eye, it introduces a distributed focus powers and spherical aberrations across pupil of an eye on top of a refractive correction for myopia, hyperopia, astigmatism across pupil of an eye.

By taking into account a typical spherical aberration in a natural eye, Liang described in the copending International application with the serial number PCT/US08/81421 a number of embodiments for distributed focus powers and spherical aberrations across the pupil of an eye. In one embodiment, significant negative spherical aberration is induced in the pupil center while a positive spherical aberration is induced at pupil periphery. In another embodiment, significant negative spherical aberration is induced in the pupil center while spherical aberration for a large pupil in an individual eye is eliminated. In yet another embodiment, positive spherical aberration is induced in the pupil center while spherical aberration for a large pupil of an eye is corrected. In an additional embodiment, spherical aberration is induced in the pupil center while spherical aberration in an eye is not altered by the correction devices. A special focus offset between the central section and outer section is required.

The outer diameter of 61 is 5 mm to 7 mm for implantable lenses like Intra-Ocular Lenses (IOLs), 1.5 mm to 6 mm for refractive corneal inlays, 10 mm to 14 mm for contact lenses, and up to 50 mm for spectacles.

FIG. 6B shows a schematic diagram of an additional embodiment of a refractive element (64) to be worn on or implanted in the eye for refractive correction of presbyopia. The refractive element comprises two transparent optical sections with a distributed focus powers and spherical aberrations, and a light attenuating segment between the two transparent optical sections.

The difference between the refractive elements in FIG. 6A and in FIG. 6B is the insertion of the light attenuating section 66 between the central aspheric section 65 and outer section 67. The light attenuating section can reduce or block light in an annular pupil section between ~3 mm and ~6 mm in order to reduce or eliminate impacts of high-order aberrations in individual eyes. Adding the light attenuating section can make the refractive element suitable for a variety of eyes with different high-order aberrations, and thus improve efficiency and efficacy of a refractive procedure.

III. Refractive Correction of Presbyopia by Creating Spherical Aberration in Central Pupil, Bifocal in Mid-Pupil, and Mono-Focal at Pupil Periphery Refractive corrections of presbyopia can further be achieved by mixing various design features to achieve the highest degree of tolerance. In the pupil periphery for night vision, it is desirable to have a single dominated focus power for far vision. In the pupil center for outdoor vision and for day vision for eyes with small pupil, it is desirable to have excellent far vision and acceptable near vision, which can be achieved by inducing spherical aberration at the central pupil. In the mid-pupil for indoor vision, it is desirable to have excellent near vision for reading and intermediate distance, which can be achieved by a bi-focal structure. Another advantage of the bi-focal structure in the mid-pupil is its insensitivity to displacement if the bi-focal lens is achieved by a structure with an alternating powers.

Figure 7A:
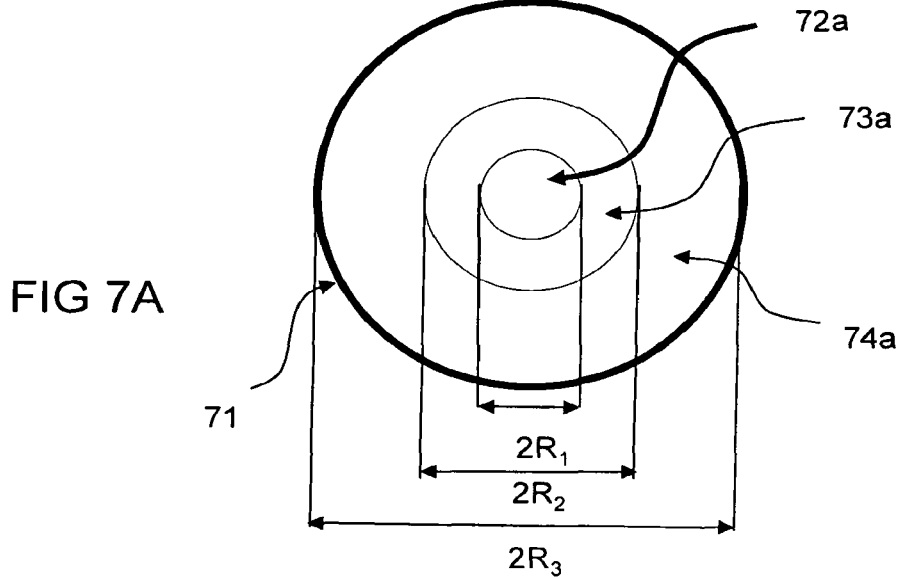
FIG. 7A shows a schematic diagram of a refractive element that can be worn on or implanted into an eye for refractive correction of presbyopia.
Figure 7B:
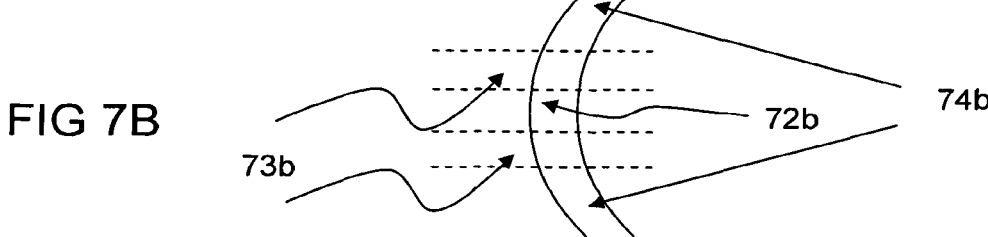
FIG. 7B shows a side view of the refractive element in FIG. 7A that can be worn on or implanted into an eye for refractive correction of presbyopia.
Figure 7C:
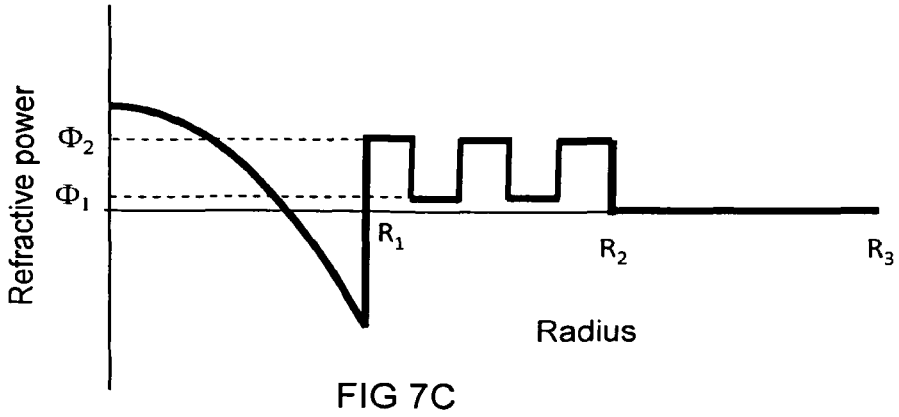
FIG. 7C shows a radial distribution of refractive power for the refractive element in FIG. 7A in one embodiment.
Figure 7D:
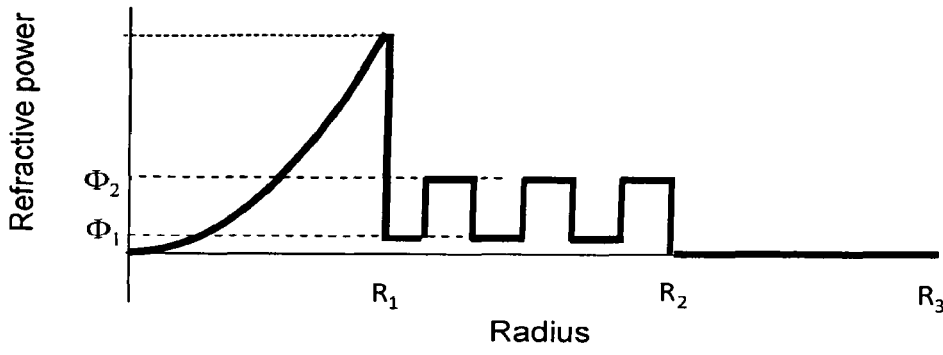
FIG. 7D shows a radial distribution of refractive power for the refractive element in FIG. 7A in another embodiment.
Figure 7E:
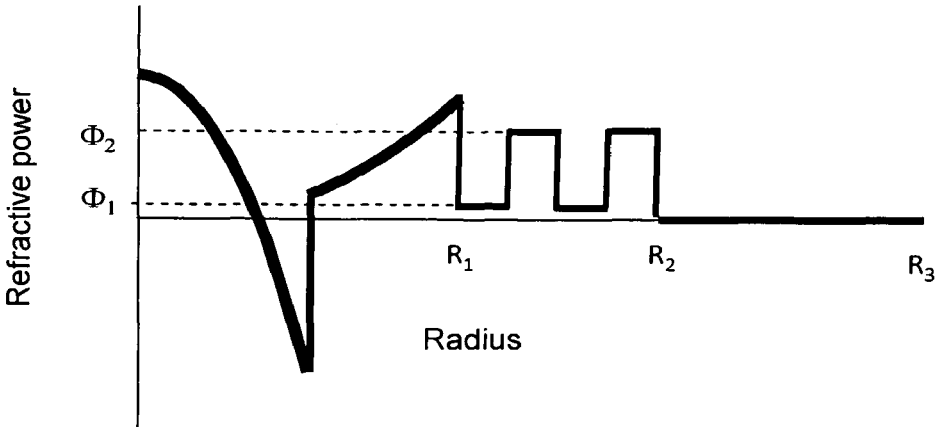
FIG. 7E shows a radial distribution of refractive power for the refractive element in FIG. 7A in yet another embodiment.

FIG. 7A and FIG. 7B shows a schematic diagram and a side view of a refractive element 71 that can be worn on or implanted into an eye for refractive correction of presbyopia according to the present invention. The central portion of the lens 72a and 72b will have at least one aspheric surface to induce spherical aberration. Three potential structures are shown with the refractive power profiles from the lens center to the radius of the central zone (R1) relating to positive spherical aberration in FIG. 7C, negative spherical aberration in FIG. 7D, and a distribution of spherical aberrations in FIG. 7E.

The middle section of the lens 73a and 73b will be a bifocal lens with a refractive power of Φ1 and Φ2. The preferred structure for the bi-focal lens is to use alternating powers from R1 to R2 shown in FIG. 7C, 7D and 7E. Depending on the preference of the lens design, Φ1 can be zero for a biasing to far vision or can be a positive number like 1D for a biased vision at intermediate distance. Φ2 is desired to be in the range from 1 Diopter or 4 Diopters depending on individual preference.

The outer section of lens 74a and 74b will be a mono-focal lens. Three structures can be designed based on the spherical aberration of an eye without the correction lens. If the eye has no spherical aberration at the pupil periphery, the outer section can be a mono-focal lens with a refractive power set for far vision. If the eye has significant spherical aberration at the pupil periphery, a bias power can be applied to the outer section for optimized for far vision at night. It is also possible to produce a lens with spherical aberration at the lens periphery to cancel out the spherical aberration at eye's pupil periphery for improved night vision.

Further devices, methods, and contemplations are provided in our co-pending PCT application with the serial number PCT/US08/81421 titled "Methods and devices for Refractive treatments of presbyopia", which was filed Oct. 28, 2008, and which is incorporated by reference herein.

Thus, specific embodiments and applications of treatment of presbyopia have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. A method for treating presbyopia of an eye, comprising:
obtaining a baseline refractive correction; and
providing a lens for wearing on the eye to create a spherical aberration or a distribution of spherical aberrations beyond the baseline refractive correction in an area of a pupil having a diameter of 1.5 mm to 3.6 mm that has negligible spherical aberration without the lens;

wherein the lens comprises:

i) an inner optical section of 1.5 mm to 3.6 mm in diameter corresponding to the area of the pupil, wherein the inner optical section comprises at least one aspheric surface, and the aspheric surface is configured to create the spherical aberration or the distribution of spherical aberrations in addition to a spherical focus power, wherein the lens is configured to have a circular shape with a radial distance expressed by r, and wherein the lens is further configured to have a thickness profile in the inner optical section that is expressed at least in part by $r^4$ to allow creation of the spherical aberration or the distribution of spherical aberrations;

ii) a middle optical section having an outer diameter of 2.5 mm to 5 mm, wherein the middle optical section is configured as a bi-focal lens; and iii) an outer optical section having an outer diameter of 4 mm to 40 mm, wherein the outer optical section is configured to have the baseline refractive correction.

2. The method of claim 1, wherein the spherical aberration or the distribution of spherical aberrations allows production of a focus variation selected from the group consisting of (a) setting a far point at a center of the lens and having a radially increased refractive power, (b) having a radially decreased refractive power and setting a portion of the eye for hyperopia, and (c) having at least one zone with a radially increased refractive power and another zone with a radially decreased refractive power and setting a portion of the eye for hyperopia.

3. The method of claim 1, wherein the lens is configured such that the spherical aberration or the distribution of spherical aberrations allows production of a focus variation of more than 4 diopters.

4. The method of claim 1 wherein the lens is further configured to allow production of a cylindrical refractive power.

5. The method of claim 1, wherein the bi-focal lens comprises alternating powers.

6. A method for refractive treatment of presbyopia, comprising:

obtaining a baseline refractive correction; and providing an optical device for wearing on an eye to induce a spherical aberration or a distribution of spherical aberrations beyond the baseline refractive correction in an area of a pupil that has negligible spherical aberration without the optical device;

wherein the optical device comprises i) an inner transparent optical section that comprises at least one aspheric surface that is configured to allow the induction of the spherical aberration or the distribution of spherical aberrations in addition to a spherical focus power, wherein the inner transparent optical section corresponds to the area of the pupil, wherein the optical device is configured to have a circular shape with a radial distance expressed by r, and wherein the optical device is further configured to have a thickness profile in the inner transparent optical section that is expressed at least in part by $r^4$ to allow creation of the spherical aberration or the distribution of spherical aberrations;

ii) a middle section that is configured to allow attenuation or blocking of light energy; and iii) an outer transparent optical section that is configured to provide at least the spherical focus power for far vision at night.

7. The method of claim 6, wherein the optical device is configured such that the spherical aberration or the distribution of spherical aberrations allows production of a focus variation selected from the group consisting of (a) setting a far point at a center of the optical device and having a radially increased refractive power, (b) having a radially decreased refractive power and setting a portion of the eye for hyperopia, and (c) having at least one zone with a radially increased refractive power and another zone with a radially decreased refractive power and setting a portion of the eye for hyperopia.

8. The method of claim 6, wherein the optical device is configured such that the spherical aberration or the distribution of spherical aberrations allows production of a focus variation of more than 4 diopters.

9. The method of claim 6, wherein the inner transparent optical section has a diameter of between 1.5 mm and 3.6 mm.

10. The method of claim 6, wherein an outer diameter of the middle section is between 2.5 mm and 5 mm.

11. The method of claim 6, wherein an outer diameter of the outer transparent optical section is between 4 mm and 40 mm.

12. The method of claim 6, wherein the optical device is configured to produce a cylindrical refractive power.

13. A method for treatment of presbyopia of an eye, comprising:

obtaining a baseline refractive correction; and providing a lens for wearing on the eye to induce a spherical aberration or a distribution of spherical aberrations beyond the baseline refractive correction in an area of a pupil of a diameter of 1.5 mm to 4 mm that has negligible spherical aberration without the lens;

wherein the lens comprises:

i) an inner optical section having a diameter of 1.5 mm to 4 mm and comprising at least one aspheric surface that is configured to allow the induction of a) the spherical aberration, wherein the induced spherical aberration covers a zone in the diameter between 1.5 mm and 4 mm, or b) the distribution of spherical aberrations in the form of a positive spherical aberration in a first zone and a negative spherical aberration in a second zone, wherein the first zone and the second zone are concentric and have a largest outer diameter equal to or less than 4 mm; in addition to a spherical focus power in the area of the pupil, wherein the lens is configured to have a circular shape with a radial distance expressed by r, and wherein the lens is further configured to have a thickness profile in the inner optical section that is expressed at least in part by $r^4$ to allow creation of the spherical aberration or the distribution of spherical aberrations; and ii) an outer transparent optical section having a diameter of 4 mm to 40 mm, wherein the outer transparent optical section is configured to have at least the spherical focus power for far vision at night or the baseline refractive correction.

14. The method of claim 13, wherein the lens is configured such that the spherical aberration or the distribution of spherical aberrations allows production of a focus variation for more than 4 diopters in a manner selected from the group consisting of (a) setting a far point at a center of the lens and having a radially increased refractive power, (b) having a radially decreased refractive power and setting a portion of the eye for hyperopia, and (c) having at least one zone with a radially increased refractive power and another zone with a radially decreased refractive power and setting a portion of the eye for hyperopia.

* * * * *